United States Patent [19]

Seki et al.

[11] Patent Number: 5,318,908
[45] Date of Patent: Jun. 7, 1994

[54] METHOD FOR CULTIVATION OF NITRILE HYDRATASE-PRODUCING PSEUDOMONAS

[75] Inventors: Susumu Seki; Masaru Suto; Koichiro Ryuno; Hitoshi Shimizu; Takanori Fujimoto, all of Yokohama, Japan

[73] Assignee: Nitto Kagaku Kogyo Kabushiki Kaisha, Tokyo, Japan

[21] Appl. No.: 735,720

[22] Filed: Jul. 26, 1991

Related U.S. Application Data

[63] Continuation of Ser. No. 454,744, Dec. 20, 1989, abandoned.

[30] Foreign Application Priority Data

Dec. 28, 1988 [JP] Japan .................. 63-329333

[51] Int. Cl.⁵ .............................. C12N 1/20
[52] U.S. Cl. ................. 435/253.3; 435/874; 435/129; 435/227
[58] Field of Search ............ 435/253.3, 874, 129, 435/227

[56] References Cited

U.S. PATENT DOCUMENTS

| | | | |
|---|---|---|---|
| 4,390,631 | 6/1983 | Watanabe et al. | 435/129 |
| 4,555,487 | 11/1985 | Yamada et al. | 435/435 |
| 4,629,700 | 12/1986 | Prevatt et al. | 435/227 |
| 4,637,982 | 1/1987 | Yamada et al. | 435/129 |
| 4,661,456 | 4/1987 | Yamada et al. | 435/244 |
| 4,661,457 | 4/1987 | Yamada et al. | 435/244 |
| 4,851,342 | 7/1989 | Watanabe et al. | 435/129 |
| 4,880,739 | 11/1989 | Yamada et al. | 435/253.3 |

*Primary Examiner*—Douglas W. Robinson
*Assistant Examiner*—Michael V. Meller
*Attorney, Agent, or Firm*—Emmanuel J. Lobato; Robert E. Burns

[57] ABSTRACT

A method for the cultivation of bacteria of the genus Pseudomonas capable of producing nitrile hydratase is disclosed. The method involves adding a water soluble copper compound in an amount of about 0.5 to 5.0 mg/l as calculated in terms of copper to a culture medium in the preparation of cells of the bacteria under shear force supplied by stirring blades, wherein the circumferential speed of the edges of the stirring blades exceeds about 2.5 m/sec. The water soluble copper compound is preferably copper chloride, copper sulfate, copper nitrate, copper acetate, copper tartrate, copper (II) acetylacetonate or copper (II) ETDA.

5 Claims, No Drawings

METHOD FOR CULTIVATION OF NITRILE HYDRATASE-PRODUCING PSEUDOMONAS

This is a continuation of application Ser. No. 07/454,744, filed Dec. 20, 1989 now abandoned.

BACKGROUND OF THE INVENTION

The present invention relates to a method of producing in a high yield and in a large amount cells of bacteria of the genus Pseudomonas having a high nitrile hydratase activity.

In recent years, there have been increasing attempts to utilize microorganisms and enzymes as they are or in immobilized state as catalysts for various single or complex chemical reactions.

Nitrile hydratase is known as an enzyme capable of hydrating nitriles to produce the corresponding amides. (Reference: Agric. Biol. Chem. 46 1165(1982)) As one example of the utilization of this enzyme, a method for preparation of amides from nitriles having 2 to 4 carbon atoms in the presence of bacteria having nitrile hydratase has been proposed. (References: Japanese Patent Pub. No. 37951/1984, U.S. Pat. No. 4,637,982 and Agric. Biol. Chem. 46 1183(1982))

Further, several methods for cultivation of such bacteria have been proposed. (Japanese Patent Pub. No. 43996/1986, No. 43997/1986, No. 43998/1986, No. 43999/1986, EP 0109083, U.S. Pat. No. 4,661,457, No. 4,661,456 and No. 4,555,487)

In order to utilize bacteria having nitrile hydratase activity on a commercial scale, it is necessary to produce bacteria in a large amount and hence to scale up a cultivation tank suitably from an experimental tank of the beaker scale.

The bacteria of the genus Pseudomonas capable of producing nitrile hydratase must be cultivated under aerobic conditions (at an oxygen feed rate of about 3.5 kg-$O_2$/$m^3$·hr.), for example, by agitation under aeration for proliferation of cells and expression of the activity thereof. When these bacteria were cultivated in a large-volume, i.e., scaled up, cultivation tank, however, both the cell concentration after completion of the cultivation and the specific activity of the cells were lower than those obtained in a breaker-scale tank, the cultivation tank could not be smoothly scaled up, and the expression of the nitrile hydratase activity was insufficient.

While the causes for such phenomena are not clear, increased shear force of stirring blades due to the scaling up of the cultivation tank required to thereby maintain the above oxygen feed rate during cultivation may not be considered to have some influence on the growth of the bacteria directly or indirectly. In any case, the bacteria of the present invention cannot be cultivated on a commercial scale unless these problems are settled.

SUMMARY OF THE INVENTION

An object of the present invention is to settle the foregoing problems, and this object has now been accomplished by a very simple and practical means which does not require modifications of the structure of the cultivation tank, i.e., by adding trace amounts of a water-soluble copper compound to a culture medium.

Thus, the method for cultivation of bacteria of the genus Pseudomonas according to this invention comprises adding a water-soluble copper compound to a culture medium in the preparation of cells of bacteria having nitrile hydratase activity by cultivating under shear force Pseudomonas bacteria capable of producing nitrile hydratase.

In the method for cultivation of Pseudomonas bacteria, the expression of the nitrile hydratase activity is remarkably improved by adding copper ion to the culture medium in accordance with the present invention as described above during the cultivation of the bacteria used herein particularly in a cultivation tank of a large volume, for example, 500 l or more as on an ordinary commercial scale in this field of art, wherein the culture system is stirred with stirring blades.

As will be apparent from the results of Example set forth hereinlater, the addition of a water-soluble copper compound in the case where a 700-l cultivation tank was used surprisingly increased the nitrile hydratase activity per unit culture fluid after 48 hours' cultivation to 2.35 times the activity attained when no such compound was added.

This increase in nitrile hydratase activity per unit culture fluid may be traceable to the increase in cell concentration and in activity of the cells per se, but the advantages appurtenant to the addition of a water-soluble copper compound are so unique that they have been least expected from the results of beaker-scale cultivation such as shake culture in a flask.

DETAILED DESCRIPTION OF THE INVENTION

Pseudomonas bacteria

The bacteria used in the present invention are those of the genus Pseudomonas having nitrile hydratase activity and the capability of hydrating nitriles, especially acrylonitrile, to produce the corresponding amides, especially acrylamide. Specific examples of such bacteria are *Pseudomonas chlororaphis* B23 (FERM BP-187) and Pseudomonas sp. PSL (FERM BP-188) disclosed in Japanese Patent Pub. No. 37951/1984 and U.S. Pat. No. 4,637,982 mentioned earlier. The details of these bacteria are given in the patent publication and the patent.

Water-soluble copper compound

The water-soluble copper compounds used in the present invention are typically inorganic salts, organic acid salts and complex salts of copper, such as copper chloride, copper sulfate, copper nitrate, copper acetate, copper tartrate, copper (II) acetylacetonate, and copper (II) EDTA. These compounds may be added singly or in a mixture to the culture medium in an amount of about 0.5 to 5 mg/l, preferably about 1 to 3 mg/l as calculated in terms of copper.

Cultivation

The cultivation according to the present invention is ordinarily carried out in a 500-l or larger cultivation tank in the presence of a water-soluble copper compound under aerobic conditions by inoculating bacteria of the genus Pseudomonas having nitrile hydratase activity into a culture medium containing: carbon sources such as glucose, fructose, sucrose, dextrin, glycerol, ethanol, and succinic acid; nitrogen sources such as ammonia, ammonium sulfate, ammonium chloride, ammonium nitrate, and urea; organic nutrient sources such as yeast extract, meat extract, malt extract, casein hydrolysate, and peptone; inorganic nutrient sources such as phosphates, magnesium salts, potassium salt, iron salts, and trace amounts of other metal salts; and enzyme inducers such as acrylamide, methacrylamide, crotonamide, n-butyramide, propionitrile, isobutyronitrile, propionamide, and isobutyramide.

The pH of the culture medium is of the order of 6 to 9, preferably of the order of 7 to 8, while the cultivation temperature is of the order of 20° to 37° C., preferably of the order of 25° to 30° C., the aeration conditions are about 0.5 to 1.0 vvm, and the cultivation time is about 1 to 3 days.

The shear force given to the culture system, which increases as the volume of the cultivation tank and the diameter of the stirring blades associated therewith increase, can be generally determined in terms of the circumferential speed of the edges of the stirring blades. This circumferential speed may vary depending on the rotational speed, shape, size and the like of the stirring blades, but is ordinarily about 2.5 to 3.0 m/sec. in the case of a 500-l tank and about 3.0 to 4.0 m/sec. in the case of a 1,000-l tank. The addition of a water-soluble copper compound according to the present invention is especially effective in such a system that the circumferential speed of the edges of stirring blades exceeds about 2.5 m/sec.

After completion of the cultivation, the bacterial cells or nitrile hydratase can be collected or utilized following the disclosures of Japanese Patent Pub. No. 37951/1984 and U.S. Pat. No. 4,637,982 mentioned previously or the Example set forth hereinafter.

Experimental Examples

Example 4.3 l of a culture fluid obtained from Pseudomonas chlororaphis B23 (FERM BP-187) grown under the following precultivation conditions was cultivated under the subsequent cultivation conditions to determine the nitrile hydratase activity of the bacteria.

1. Cultivation of Bacteria
(1) Precultivation Conditions
Composition of culture medium (pH 7.2):

| peptone | 5 g/l |
| yeast extract | 3 g/l |
| malt extract | 3 g/l |
| glucose | 5 g/l |

Cultivation temperature: 25° C.
Aeration/Agitation: 1 vvm/200 rpm
Cultivation time: 24 hours
Volume of cultivation tank: 20 l (245φ×450 L)
Quantity of culture fluid charged: 13 l
Stirrer: stirrer with one six-bladed disc turbine (115 φ)
(2) Cultivation Conditions
Composition of culture medium (pH 7.8):

| sucrose | 30 g/l |
| MIEKI ®* | 20 g/l |
| methacrylamide | 9.5 g/l |
| MgSO$_4$.7H$_2$O | 1 g/l |
| FeSO$_4$.7H$_2$O | 0.05 g/l |

-continued

| K$_2$HPO$_4$ | 1 g/l |

2. Measurement of Nitrile Hydratase Activity 0.1 ml of a culture fluid and 4.90 ml of 1/20M phosphate buffer (pH 7.7) were mixed together, and 5 ml of 1/20M phosphate buffer (pH 7.7) containing 5.0% by weight of acrylonitrile was added. The mixture was caused to react at 10° C. for 10 minutes and filtered to separate bacterial cells. The nitrile hydratase activity of the cells was determined by measuring the quantity of the acrylamide (AA) produced by means of gas chromatography.

The results obtained after 48 hours' cultivation were as shown in the following TABLE.

The activity was determined for the specific activity (S.A.) and the total activity (T.A.) as defined below.
S.A.: μmole AA/mg-cells/min.
T.A.: μmole AA/ml-culture fluid/min.

Comparison Example

Cultivation was carried out under the same conditions as in the preceding Example except that CuSO$_4$.5H$_2$O was not added to the culture medium.

The results obtained in this Comparison Example after 48 hours' cultivation are also shown in the following TABLE.

TABLE

| | Cell concentration (g/l) | S.A. | T.A. (relative value) |
|---|---|---|---|
| Comparison Example | 9.96 | 59.9 | 597 (100) |
| Example | 14.40 | 97.4 | 1402 (235) |

We claim:

1. A method for the cultivation of bacteria of the genus Pseudomonas capable of producing nitrile hydratase which comprises adding a water soluble copper compound in an amount of about 0.5 to 5 mg/l as calculated in terms of copper to a culture medium in the preparation of cells of said bacteria under shear force supplied by stirring blades, wherein the circumferential speed of the edges of the stirring blades exceeds about 2.5 m/sec.

2. The method as claimed in claim 1, wherein the water-soluble copper compound is selected from the group consisting of copper chloride, copper sulfate, copper nitrate, copper acetate, copper tartrate, copper (II) acetylacetonate, and copper (II) EDTA.

3. The method as claimed in claim 1, wherein the amount of the water-soluble copper compound added to the culture medium is about 1 to 3 mg/l as calculated in terms of copper.

4. The method as claimed in claim 1, wherein the cultivation of bacteria of the genus Pseudomonas is carried out on a commercial scale.

5. The method as claimed in claim 1, wherein the cultivation of bacteria of the genus Pseudomonas is carried out in a cultivation tank having a volume of at least 500 liters.

* * * * *